United States Patent [19]

Kuno

[11] Patent Number: 4,902,432
[45] Date of Patent: Feb. 20, 1990

[54] TREATING METHOD OF PREVENTING PUTREFACTION AND EMISSION OF RANCIDITY OF WATER-CONTAINED CUTTING OR GRINDING OIL AND TREATING BAG MEMBER FOR USE IN THE SAME

[75] Inventor: Toyohiko Kuno, Kyoto, Japan

[73] Assignee: Kinki Pipe Giken Kabushiki Kaisha, Kyoto, Japan

[21] Appl. No.: 311,160

[22] Filed: Feb. 15, 1989

[51] Int. Cl.$^4$ .................................................. C02F 1/68
[52] U.S. Cl. ...................................... 210/764; 210/501
[58] Field of Search ............... 210/749, 753, 754, 757, 210/758, 764, 501; 71/67; 252/175, 176, 178; 514/187, 191, 576; 560/87

[56] References Cited

U.S. PATENT DOCUMENTS

| | | | |
|---|---|---|---|
| 4,095,029 | 6/1978 | Fields | 252/354 |
| 4,602,011 | 7/1986 | West et al. | 514/187 |
| 4,766,113 | 8/1988 | West et al. | 514/187 |

*Primary Examiner*—Frank Sever
*Attorney, Agent, or Firm*—Koda & Androlia

[57] ABSTRACT

A treating method of preventing the putrefaction and emission of rancidity of water-contained cutting or grinding oil by placing in the oil a treating bag member wherein solids comprised of water-soluble glass composition containing $Ag^{30}$ ion in the composition thereof are wrapped in water-permeable fiber cloth. The method makes it possible to suppress the development of microbes forming which cause the putrefaction and rancidity of oil by the action of $Ag^{30}$ ion so as to prolong the service period of the oil by a substantial degree and also to stabilize the effect by making $Ag^{30}$ ion flow out in generally constant relation with lapse of time.

10 Claims, 2 Drawing Sheets

TREATING METHOD OF PREVENTING PUTREFACTION AND EMISSION OF RANCIDITY OF WATER-CONTAINED CUTTING OR GRINDING OIL AND TREATING BAG MEMBER FOR USE IN THE SAME

BACKGROUND OF THE INVENTION

1. Field of the Invention

This invention relates to a treating method of preventing putrefaction of and removing the rancidity of cutting oil or grinding oil used in cutting or grinding work and to a treating bag member for use in the method.

2. Prior Art

Cutting oil and grinding oil have heretofore been widely used in the field of various machining works. Recently, there is an increasing tendency of water-contained oils having come to be used owing to increased high-speed of cutting and grinding conditions, advanced tool technique, sense of saving on resources, improvement in oil itself, and so on.

These water-contained cutting and grinding oils contain a variety of organic substances in their constituents, and are used by being diluted with water in time of machining work, along with which abrasive powder, bonding agent and the like are mixed into the oils.

But the water-contained cutting oil and grinding oil, after they have been diluted with water, proliferate bacteria and mold because of temperature rise consequent upon each machining work, decomposed constituents of additives in the oils, and the like, and gradually cause their putrefaction and come to emit rancidity. And when putrefaction progresses, the problem pops up that the oils themselves are polluted or formed with slime by the action of bacteria to reduce the circulation of oils and thus not only to aggravate work site environment due to emission of racidity but also to reduce the service life of machine tools intended for machining.

In view of the circumstances above, Japanese Patent Publication Laid-open No.210098/1987 disclosed a water treating agent consisting of water-soluble glass containing $Ag^+$ ion in its composition. The agent is designed to kill germs and microorganisms by the agent making the $Ag^+$ ion gradually flow out in the water in accordance with dissolution of the glass in the water, and according to this prior art, the agent of the kind described is directed to reduction or removal of germs and microorganisms in the water such as circulation water in a cooling tower, reservoir water in a swimming pool, and the like. But the prior art not only makes no experiment with its application to the prevention intended by this invention of the putrefaction and rancidity of the water-contained cutting and grinding oils but also makes no disclosure of suggestion of such application.

But when glass is nakedly steeped in the water directly as is done in the prior art, the glass combines with the inorganic ion (Fe, Ca, Mg, etc.) in the water to partially form a water-insoluble film on the surface of the glass either to render its dissolution in the water difficult or to make suspended matter and floating substances in the water attach to the surface of the glass to reduce solubility of glass, making it ultimately difficult to expect the stability of effects provided by uniform and continuous dissolution of the glass.

SUMMARY OF THE INVENTION

Thus, in an attempt to obviate the disadvantages inherent in the prior art, the invention has for its object the provision of a novel method of preventing the putrefaction and emission of rancidity of the cutting or grinding oil by the water-soluble glass containing monovalent Ag and enveloped in water-permeable fiber cloth and the provision of a treating bag member for use in the method.

A detailed description will now be given of embodiments of the invention shown by way of example only with reference to the accompanying drawings.

DETAILED DESCRIPTION OF THE INVENTION

Figure 1:
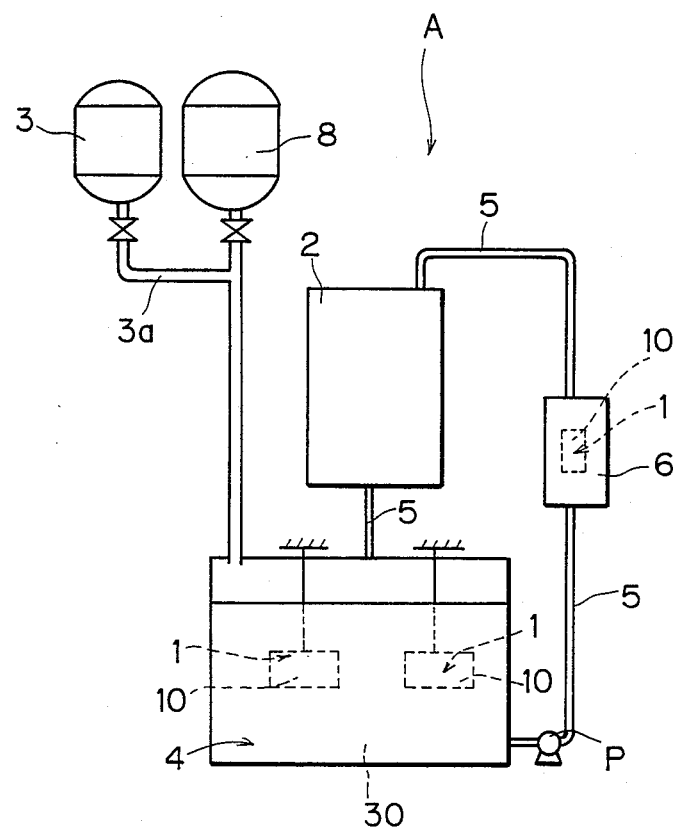
FIG. 1 schematically illustrates a closed-loop circulatory system of cutting or grinding oil according to the method of the invention.

According to the invention, there is provided a treating method of preventing the putrefaction and emission of rancidity of water containing cutting and grinding oils wherein, as shown in FIG. 1, a solid 10 comprised of any one or a mixture of lumps, granules and powders of water-soluble glass containing monovalent Ag in the composition thereof is wrapped in water-permeable fiber cloth 1 and steeped in cutting or grinding oil 30 diluted with water within an oil circulatory system A to dissolve the glass solids 10 inside the wrapping fiber cloth 1 in the water through a gelled state of the glass to make $Ag^+$ ion flow out into the water and hold the dissolved $Ag^+$ ion in the gelled glass while preventing suspended substances and floating solids contained in the oil from infiltrating through the texture of the water-permeable fiber cloth 1 by the use of fine texture, and thereafter the $Ag^+$ ion is allowed to flow out gradually through the texture of the cloth 1 into the rest of water outside the cloth 1 within the oil circulatory system A.

On the other hand, according to the invention, there is also provided a treating bag member wherein, as shown in FIG. 2, a solid 10 comprised of any one or a mixture of lumps, granules and powders of water-soluble glass containing monovalent Ag in the composition thereof is wrapped in the water-permeable fiber cloth 1.

The water-soluble glass solid is comprised of one or more than two kinds of mesh-forming oxides of $SiO_2\omega_2O_3$ and $P_2O_5$, or one or more than two kinds of mesh-modifying oxides of $Na_2O$, $K_2O$, $CaO$, $MgO$, $BaO$ and $ZnO$, and one or two kinds of intermediate oxides of $Al_2O_3$ and $TiO_2$ and contains 0.1–2.5 parts by weight of monovalent Ag, for example $Ag_2O$ in 100 parts by weight of this solid and is so regulated that the amount of the solid added to the water content of the cutting or grinding oil may amount to 300–1000 g/m$^3$.

Referring now to the effects of the invention, the glass solid 10 containing monovalent Ag in the composition thereof is wrapped in the water-permeable fiber cloth 1 and is steeped in the water-contained cutting or grinding oil so that the glass solid 10 is dissolved in a gelled state inside the fiber cloth 1 to keep back the solid 10 from rapidly flowing out of the cloth and is gradually dissolved to flow out $Ag^+$ ion to make the thus gelled substance hold the Ag+ ion therein little by little, whereafter the Ag+ ion gradually flows out through the texture of the fiber cloth 1 into the rest of water outside the cloth 1 to thereby prevent the water-contained cutting or grinding oil from putrefying and emitting rancidity by the germiciding and deodorizing effects of the Ag+ ion on microorganisms, mold or the like. The effects control the velocity of dissolution of the solid 10 in the water by gelation of the solid to thereby permit the Ag+ ion to flow out in the water under continued retention of a given quantity of Ag+ ion in the water through lapse of time.

At this juncture, consideration is given to the texture of the cloth 1 so as to prevent the infiltration of the suspended substances and suspended solids contained in the oil through the texture of the cloth 1 to provide Ag+ ion effect with high efficiency.

Incidentally, it is desirable to use nonwoven fabric as the water-permeable fiber cloth 1 when the cloth is used in the cutting oil and to use woven fabric or synthetic resin sheet when the fiber cloth 1 is used in the grinding oil.

PREFERRED EMBODIMENTS OF THE INVENTION

A description will now be given of the method according to the invention and of the treating bag member used therein by way of example only.

The method of the invention is intended for use as in an oil circulatory system A comprises a closed-loop pipe 5 for oil adapted for cutting or grinding machine tools such as shown in FIG. 1. In the drawings, the numeral 3 designates a fresh oil for storing cutting or grinding oil therein to feed the oil through a pipe 3a to an oil reservoir (to be referred to hereinafter as "reservoir"). The cutting oil or grinding oil is an oil prepared by adding various chemicals and organic substances to mineral oil such as spindle oil and machine oil, and is used in circulation thereafter by being diluted to 10–100 times with water stored in a suitable water tank 8.

Namely, the cutting or grinding oil which is supplied from the reservoir 4 through the pipe 5 to a cutting or grinding machine 2 for cutting or grinding a tool flows back again into the reservoir 4 and is temporarily stored therein. As shown, a water-soluble glass solid 10 containing monovalent Ag is wrapped in a water-permeable fiber cloth 1 and is suspendedly steeped in the reservoir 4.

As for the water-permeable fiber cloth 1, it is preferred that a nonwoven fabric of synthetic fiber such as nylon and Tetlon be used in cutting oil relatively small, for example, in the amount of abrasive powder added and that a woven or nonwoven fabric of synthetic fibers such as polyethylene, polyester and a synthetic fiber sheet be used in grinding oil having abrasive powder added thereto in large quantities.

In order to effectively prevent the putrefaction and emission of rancidity of the oil by Ag+ ion in the glass 10, the water-permeable fiber cloth 1 having the soluble glass solids wrapped therein is suspendedly steeped purally or singly for example in the intermediary position of the reservoir 4 as shown in such manner as to bring the glass solids 10 into contact with the oil relative to the cloth 1 in the oil reservoir 4 in all directions of the cloth.

The water-soluble glass solids 10 wrapped in water-permeable fiber cloth 1 may also be placed likewise in a treatment unit 6 provided in the flow course of cutting or grinding oil returned in the direction of an oil tank 3, independently of the reservoir 4, for example from the reservoir 4 by a pump P so as to bring the circulating oil into contact with the water-permeable fiber cloth 1 wrapping the solids.

In the description above, it is clearly shown that the cutting or grinding oil protects against putrefaction and emission of rancidity by the fiber cloth 1 containing the water-soluble glass solids 10 therein being suspendedly steeped in the reservoir 4 during the circulation course of the oil the circulation course of the oil continuously fed and returned during which the oil is mixed movingly with the water. But the method according to the invention is not limited to the one illustrated, and for example, even when cutting or grinding work is temporarily stopped and the oil is placed still in the reservoir 4 to thereby bring the water-contained oil into the state of two separated layers of water and oil, the prevention by the glass solids 10 of putrefaction and emission of rancidity relative to the water layer in the reservoir 4 is effected by the water-permeable fiber cloth 1 containing water-soluble glass solids and which is steeped suspendedly in the reservoir 4.

Referring now to a treating bag member provided by the invention and used in the above-described method of preventing the putrefaction and emission od rancidity of the water-contained cutting or grinding oil, the bag member comprises a water-soluble glass solid having a composition comprised of one or more than two kinds of $SiO_2$, $B_2O_3$ and $P_2O_5$, one or more than two kinds of $Na_2O$, $K_2O$, $CaO$, $MgO$, $BaO$ and $ZnO$, one or two kinds of $Al_2O_3$ and $TiO_2$, wherein the water-soluble glass contains 0.1–2.5 parts by weight of, for example, $Ag_2O$ as monovalent Ag in 100 parts by weight of the solid and wherein the solid 10 of such composition is provided in lumps, granules, powders or in the form of a mixture thereof and is wrapped in the water-permeable fiber cloth 1.

Figure 2A:
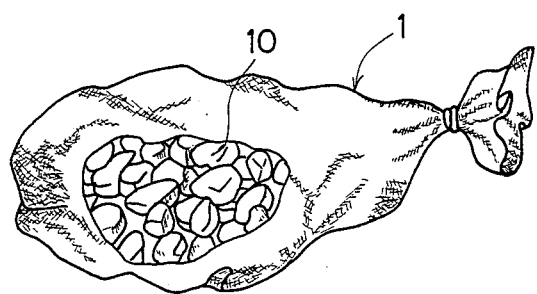
FIGS. 2a and 2b illustrate embodiments of the invention in two aspects of use of the treating bag member of the invention, respectively.
Figure 2B:
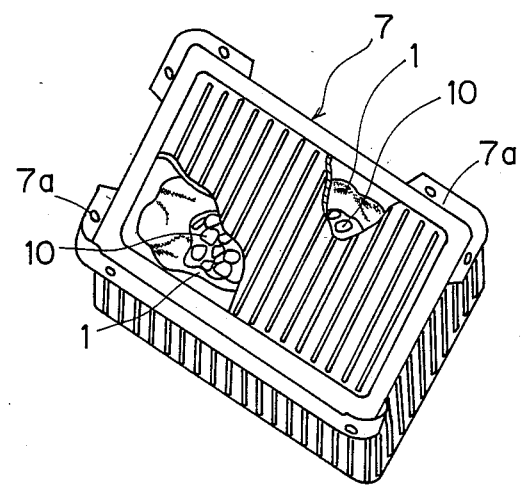

Also, in order to facilitate hanging of the cloth-enclosed solids 10 in the reservoir 4 or treatment unit 6, the water-permeable fiber cloth 1 wrapping the solids therein and shown in FIG. 2A may be used in such manner that the cloth 1 is enclosed singly or plurally in a box-type container 7 having amultiplcity of water passage openings and having projections 7a at the end as shown in FIG. 2B.

Furthermore, the amount of addition of the glass solids 10 to the water content 1 of the oil is preferably 300–1000 g/m$^3$ and Ag+ ion of the solids 10 is made to flow gradually into the oil within the range of that amount so as to have the Ag+ ion regulated to ultimately amount to 3–5 ppm to thereby effect the intended prevention of putrefaction and emission of rancidity of the oil.

Next, Table 1 shows the result of test conducted on the prevention of putrefaction of the water in the cutting oil in the reservoir by the use of the method and treating bag member according to the invention.

Namely, the test of the method was conducted by regulating the cutting oil in the reservoir in such manner that the oil had the ratio of 600 g of water-soluble glass containing monovalent Ag to 1000 l of water-contained cutting oil (emulsion type) brought into a critical state of use. The glass solids were enclosed in the nonwoven nylon fabric having a standard 10–12 mesh and were suspendedly steeped in the reservoir.

Furthermore, the monovalent Ag-contained water-soluble glass was manufactured in the manner that 0.5% by weight of monovalent Ag in terms of $Ag_2O$ was added to 40.0 mol % of $SiO_2$, 50.0 mol % of $B_2O_3$ and 10.0 mol % of $Na_2O$ and that the resulting mixture was evenly mixed, melted in a glass melting furnace at temperatures in the range of 1100°–1300° C. for 60 minutes and was rapidly cooled.

TABLE 1

| Item | cutting oil in its critical state of use | State 7 days after addition of Ag-contained soluble glass | 15 days after addition of Ag-contained soluble glass | 30 days after addition of Ag-contained soluble glass |
|---|---|---|---|---|
| Kind of device | cutting machine | cutting machine | cutting machine | cutting machine |
| pH | 8.0 | 8.2 | 8.6 | 8.6 |
| Total of living bacteria (eumycetes, germs) | $10^8$ | $10^7$ | $10^6$ | $10^5$ |
| Mold | +++ high contamination | medial contamination | medial contamination | medial contamination |
| Sulfate reducing bacteria | +++ high contamination | ++ medial contamination | ++ medial contamination | ++ medial contamination |
| Rancidity | 4 degrees (of six ranked degrees) | 2 degrees (of six ranked degrees) | 1 degree (of six ranked degrees) | 1 degree (of six ranked degrees) |

Note:
Treatment temperature 35° C.
Opened at the top of the reservoir

The test result in Table 1 shows that the method and treating bag member of the invention reduce, by lapse of time, eumycetes, mold, sulfate-reducing bacteria which form the cause of putrefaction of the water in the cutting oil, while on the other hand they promote the effect of $Ag^+$ ion and reduce the emission of rancidity by increasing pH-value on the alkali side.

In addition, Table 2 shows the result of the test conducted on the effect produced by the method and treating bag member of the invention on the removal of emission of rancidity of the water-contained grinding oil (emulsion type) in the reservoir.

Namely, the grinding oil in the reservoir was regulated in the manner that the oil might have the ratio of 400 g of water-soluble glass containing monovalent Ag prepared by the same method as above to 600 l of grinding oil (emulsion type) brought into a critical state of use. The glass solids were enclosed in the polyehylene woven fabric having a standard 12-inch mesh and which was laid in two layers one over the other and were suspendedly steeped in the reservoir.

TABLE 2

| Strength of rancidity (6 ranked degrees of rancidity representing the strength of rancidity) | | According to strength of rancidity | | Remarks |
|---|---|---|---|---|
| 6 | Powerful odor | 2.0 | ppm | Before use |
| 5 | Slightly reduced in power odor | 2.0 | ppm | 1st day after use of Ag-contained soluble glass |
| 4 | Strong odor | 0.8 | ppm | 2nd day |
| 3.5 | Slightly reduced in strong odor | 0.2 | ppm | 4th day |
| 3.5 | Considerably eased | 0.2 | ppm | 5th day |
| 3 | Can be readily sensed | 0.05 | ppm | 6th day |
| 3 | " | 0.05 | ppm | 7th day |
| 3-2.5 | Reduced greater in odor | 0.05 | ppm | 8th day |
| 3-2.5 | Same as previous day | 0.05 | ppm | 11th day |
| 2 | Slight odor | 0.002 | ppm | 13th day |
| 2 | " | 0.002 | ppm | 14th day |
| 1 | Odor scarcely sensed | 0.000 | ppm | 15th day |
| 1 | No odor | limit of test | | 20th day |
| 1 | " | " | | 30th day |

Note:
Treatment temperature 45° C.
Opened at the top of the reservoir

As apparent from the result in Table 2, the rancidity of the grinding oil is reduced day after day by the method and treating bag member of the invention.

As above, since the method of the invention prevents the putrefaction and emission of rancidity by $Ag^+$ ion flowing out into the cutting or grinding oil in accordance with the dissolution in the water-contained cutting or grinding oil of the soluble glass solids containing monovalent Ag and wrapped in the water-permeable fiber cloth, the method makes it possible to suppress by the action of $Ag^+$ ion the development of microbes which form the cause of putrefaction and emission of rancidity of the used oil and to prolong the service period of the oil in a substantial degree.

Accordingly, the method of the invention makes it possible to materialize reduction in expenses due to prolonged period of time for oil replacement and to improve working environment.

Moreover, since the treating bag member comprised of the above glass solids is not of the type which makes it necessary to place a fixed quantity of solids in the reservoir or the unit during treatment, but of the type in which mere hanging of the solids in the reservoir or the unit can serve the purpose, the bag member is not only simple in handling but also advantageous in that it does not damage nor spoil cutting and grinding machines.

I claim:

1. A treating method comprising: preventing putrefaction and emission of rancidity of water-contained cutting or grinding oil used, by wrapping a solid comprised of any one or a mixture of lumps, granules and powders of water-soluble glass composition containing monovalent Ag in the composition thereof in water-permeable fiber cloth and steeping said solid in cutting or grinding oil diluted with water to dissolve the glass inside the wrapping fiber cloth in the water through a gelled state of the glass to make $Ag^+$ ion flow out into the water and hold the $Ag^+$ ion in the gelled glass while preventing the suspended substances and suspended solids in the oil from infiltrating through the texture of the water-permeable fiber cloth, and thereafter causing the $Ag^+$ ion to flow out gradually through the texture of the fiber cloth into the rest of water outside the wrapping cloth.

2. A treating method according to claim 1 wherein the supply and discharge of the cutting oil or grinding oil to and from a cutting or grinding machine are carried out by one closed-loop pipe, respectively and said water-soluble glass solids wrapped in the water-permeable fiber cloth are steeped in the oil reservoir along the closed-loop pipe.

3. A treating method according to claim 2 wherein the water-contained cutting or grinding oil is placed still in the reservoir and separated in two layers of oil and water, and said water-permeable fiber cloth containing the water-soluble glass solids wrapped therein is suspendedly steeped in the water layer.

4. A treating method according to claim 2 wherein the water-contained cutting or grinding oil are continuously supplied and returned to the reservoir to bring the water content of the oil and the oil content thereof into a mixed state movingly, and said water-permeable fiber cloth contains the glass solids wrapped therein is suspendedly steeped in the oil.

5. A treating method according to claim 1 wherein said water-soluble glass solids wrapped in the water-permeable fiber cloth are placed in a treating unit independent of the reservoir and the unit is provided in any place along the closed-loop pipe so that the cutting or grinding oil may pass through the unit while being brought into contact with said glass solids.

6. A treating method according to claim 1 or 2 or 3 or 4 or 5 wherein said water-permeable fiber cloth wrapping said water-soluble glass solids therein are held in contact with the oil relative to the surface of the cloth in all the direction thereof.

7. A treating method according to claim 1 or 2 or 3 or 4 or 5 wherein said water-soluble glass composition is comprised of one or more than two kinds of $SiO_2$, $B_2O_3$ and $P_2O_5$, one or more than two kinds of $Na_2O$, $K_2O$, $CaO$, $MgO$, $BaO$ and $ZnO$, one or two kinds of $Al_2O_3$ and $TiO_2$, and contains 0.1–2.5 parts by weight of $Ag_2O$ in 100 parts by weight of the composition, and the glass is 300–1000 $g/m^3$ in the amount of glass added to the water.

8. A treating method according to claim 1 or 2 or 3 or 4 or 5 wherein the water-permeable fiber cloth comprises nonwoven fabric of synthetic fibers.

9. A treating method according to claim 1 or 2 or 3 or 4 or 5 wherein the water-permeable fiber cloth comprises a woven fabric of synthetic fibers or synthetic resin sheet.

10. A treating method according to claim 1 or 2 or 3 or 4 or 5 wherein the oil consisting essentially of mineral oil is diluted with about 10–100 times larger amount of water.

* * * * *